US009173736B2

(12) United States Patent
Bertini

(10) Patent No.: US 9,173,736 B2
(45) Date of Patent: Nov. 3, 2015

(54) METHOD OF MAKING AN ENDOLUMINAL VASCULAR PROSTHESIS

(75) Inventor: Timothy Bertini, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 665 days.

(21) Appl. No.: 13/096,632

(22) Filed: Apr. 28, 2011

(65) Prior Publication Data

US 2012/0277850 A1 Nov. 1, 2012

(51) Int. Cl.
*A61F 2/07* (2013.01)
*A61F 2/06* (2013.01)
*D03D 3/02* (2006.01)
*A61F 2/89* (2013.01)

(52) U.S. Cl.
CPC ... *A61F 2/07* (2013.01); *A61F 2/06* (2013.01); *A61F 2/89* (2013.01); *A61F 2002/061* (2013.01); *A61F 2002/065* (2013.01); *A61F 2002/075* (2013.01); *A61F 2240/001* (2013.01); *D03D 3/02* (2013.01); *Y10T 29/49826* (2015.01); *Y10T 156/1002* (2015.01)

(58) Field of Classification Search
CPC ............... A61F 2/07; A61F 2/04; A61F 2/06; A61F 2240/001; D03D 3/02
USPC ....... 600/36; 623/1.13, 1.51, 1.53; 139/387 R
See application file for complete search history.

(56) References Cited

U.S. PATENT DOCUMENTS

| 2,978,787 | A | * | 4/1961 | Liebig ......................... 623/1.51 |
| 4,655,771 | A | | 4/1987 | Wallsten |
| 5,413,598 | A | * | 5/1995 | Moreland ....................... 600/36 |
| 5,423,849 | A | | 6/1995 | Engelson |
| 5,476,506 | A | * | 12/1995 | Lunn ........................... 623/1.13 |
| 5,628,782 | A | * | 5/1997 | Myers et al. .................... 600/36 |
| 5,910,168 | A | | 6/1999 | Myers |
| 6,159,239 | A | * | 12/2000 | Greenhalgh ................. 623/1.13 |
| 6,689,162 | B1 | | 2/2004 | Thompson |
| 2005/0277675 | A1 | | 12/2005 | Fuugetsu |

FOREIGN PATENT DOCUMENTS

| DE | 12 65 341 B | 4/1968 | |
| WO | WO 8201647 | 5/1982 | |
| WO | WO 9725002 | 7/1997 | |
| WO | WO 9937242 A1 * | 7/1999 | ................ A61F 2/06 |

* cited by examiner

*Primary Examiner* — Brian Pellegrino

(57) ABSTRACT

A flat sheet of woven material includes warp yarns and weft yarns interlaced at substantially right angles to each other. A graft material is cut from the flat sheet of woven material such that the graft material includes a graft material longitudinal axis and the warp yarns are disposed at an angle relative to the graft material longitudinal axis. The warp yarns and weft yarns are not parallel to or perpendicular to the graft material longitudinal axis. The graft material is formed into the shape of an endoluminal prosthesis, such as by rolling opposing edges towards each other and securing the opposing edges to each other. The endoluminal prosthesis thus includes warp yarns disposed at an angle relative to the prosthesis longitudinal axis.

9 Claims, 4 Drawing Sheets

METHOD OF MAKING AN ENDOLUMINAL VASCULAR PROSTHESIS

TECHNICAL FIELD

This invention relates generally to a method of making a vascular prosthesis.

BACKGROUND

Vascular aneurysms are the result of abnormal dilation of a blood vessel, usually from disease or a genetic predisposition, which can weaken the arterial wall and allow it to expand. Aneurysms can occur in any blood vessel, but most occur in the aorta and peripheral arteries, with the majority of aneurysms occurring in the abdominal aorta. An aneurysm is at risk of rupture resulting in extravasation of blood into, for example, the peritoneal cavity or into tissue surrounding the diseased artery.

Aneurysms, especially abdominal aortic aneurysms, are commonly treated in open surgery procedures in which the diseased vessel segment is bypassed and repaired with an artificial vascular graft. While open surgery is an effective surgical technique in light of the risk of a fatal abdominal aortic aneurysm rupture, the open surgical technique suffers from a number of disadvantages. The surgical procedure is complex, requires a long hospital stay, requires a long recovery time, and has a high mortality rate. Less invasive devices and techniques have been developed to avoid these disadvantages.

In particular, aneurysm exclusion devices, such as endoluminal vascular prostheses and stent grafts, may be positioned and deployed within the affected artery through insertion catheters by percutaneous procedures in a less or minimally invasive procedure than open surgical procedures. The tubular endoluminal prosthesis is introduced in a small diameter crimped condition and expanded at the aneurysm. Aneurysm exclusion devices are used to exclude vascular aneurysms and provide a prosthetic lumen for the flow of blood. Although often referred to as stent grafts, these tubular endoluminal prostheses differ from covered stents in that they are not used to mechanically prop open natural blood vessels. Rather, they are used to secure an artificial lumen in a sealing engagement with the vessel wall without further opening the abnormally dilated natural blood vessel.

Stent grafts for use in aneurysms typically include a support structure supporting a woven graft material. Examples of textile graft materials are woven, braided, or knitted polymer or metallic materials, e.g., polyester, polytetrafluoroethylene, polypropylene, stainless steel, or nitinol. The graft material is secured to the inner or outer diameter of the support structure, which supports the graft material and/or holds it in place against a luminal wall. The stent graft is generally secured to a vessel wall above and below the aneurysm. A proximal spring stent of the stent graft can be located above the aneurysm to provide a radial force which engages the lumen wall and seals the stent graft at the lumen wall.

As noted above, the graft material in a conventional stent graft is commonly a woven textile structure. Weaving involves the interlacing of two sets of threads or yarns at right angles to each other: the warp or end yarns and the weft, fill or pick yarns. The warp yarns are held taut and in parallel order, typically by means of a loom. The loom is warped (or dressed) with the warp yarns passing through heddles on two or more harnesses. The warp yarns are moved up or down by the harnesses creating a space called the shed. The weft yarns are inserted into the shed at an angle perpendicular to the warp yarns in a process called filling. There are different types of filling mechanisms, including, for example and not by way of limitation, shuttles, rapiers, and projectiles. There are different types of weaves, including, for example and not by way of limitation, plain weaves, twill weaves, and satin weaves.

Textile structures or patterns are distinguished from other structures by the manner in which they are made. For example, a braided structure or pattern is formed by intertwining three or more strands of flexible material such as textile fibers or yarns. Compared to the process of weaving a wide sheet of cloth from two separate, perpendicular groups of strands (warp and weft), a braid is usually long and narrow, with each component strand functionally equivalent in zig-zagging forward through the overlapping mass of the others.

As shown in FIGS. 1-2, a conventional stent graft 100 includes a graft material 102. Graft material 102 is generally a woven textile product, constructed in a tubular configuration, by means of a shuttle loom, resulting in end or warp yarns 104 that run longitudinally and parallel to longitudinal axis 110 and fill or weft yarns 106 that run circumferentially. Braided textile materials are generally not suitable for stent grafts because braided materials tend to be unstable and generally too porous due to the lack of interaction between yarns. However, conventional stent grafts 100 with stent graft material 102 having warp yarns 104 running longitudinally and weft yarns 106 running circumferentially may lack flexibility in certain performance characteristics.

Accordingly, a woven graft material and method of forming an endovascular prosthesis using such a woven graft material that permits improved performance characteristics the prosthesis is needed.

SUMMARY OF THE INVENTION

Embodiments hereof describe a method of forming an endoluminal prosthesis. In one embodiment, a flat sheet of woven material includes warp yarns and weft yarns interlaced at substantially right angles to each other. A graft material is cut from the flat sheet of woven material such that the graft material includes a graft material longitudinal axis and the warp yarns are disposed at an angle relative to the graft material longitudinal axis. The warp yarns and weft yarns are not parallel to or perpendicular to the graft material longitudinal axis. The graft material is formed into the shape of an endoluminal prosthesis, such as by rolling opposing edges towards each other and securing the opposing edges to each other. The endoluminal prosthesis thus includes warp yarns disposed at an angle relative to the prosthesis longitudinal axis, wherein the warp yarns and weft yarns are not parallel to or perpendicular to the prosthesis longitudinal axis. The angle may be between 15 degrees and 75 degrees, between 30 degrees and 60 degrees, or approximately 45 degrees. At least one stent may be coupled to the graft material.

Embodiments hereof also describe an endoluminal prosthesis including a substantially tubular woven graft material including a longitudinal axis. The graft material comprises warp yarns and weft yarns interlaced at substantially right angles to each other, wherein the warp yarns are disposed at an angle relative to the longitudinal axis of the prosthesis. The angle is such that the warp yarns and weft yarns are not parallel to or perpendicular to the longitudinal axis. The endoluminal prosthesis may also include at least one stent coupled to the graft material.

BRIEF DESCRIPTION OF THE DRAWINGS

Embodiments will be further explained with reference to the accompanying drawings, which are incorporated herein and form a part of the specification. The drawings further serve to explain the principles of the invention and to enable a person skilled in the pertinent art to make and use the invention. The drawings are not to scale.

DETAILED DESCRIPTION

With reference to the accompanying figures, wherein like components are labeled with like numerals throughout the figures, illustrative graft materials for endoluminal prostheses, and methods for making endoluminal prostheses are disclosed.

Figure 1:
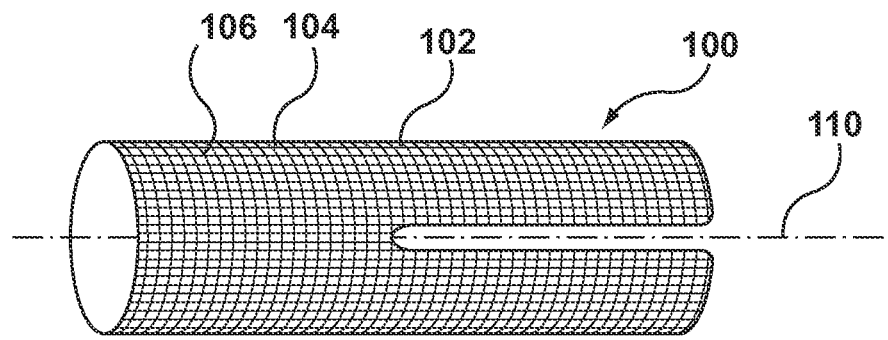
FIG. 1 is a schematic illustration of a conventional endoluminal prosthesis.
Figure 2:
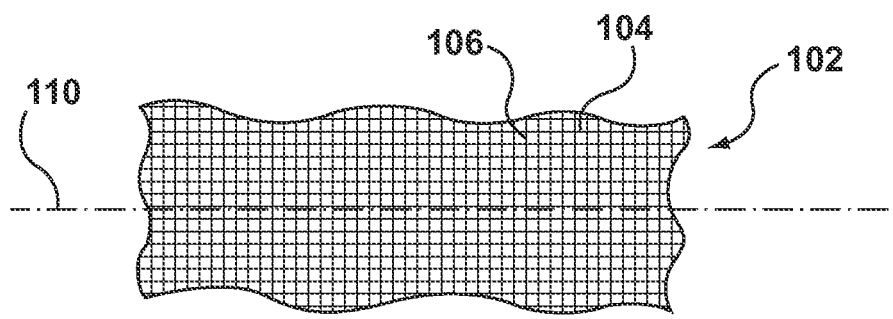
FIG. 2 is a schematic illustration of a portion of the graft material of the endoluminal prosthesis of FIG. 1.
Figure 3:
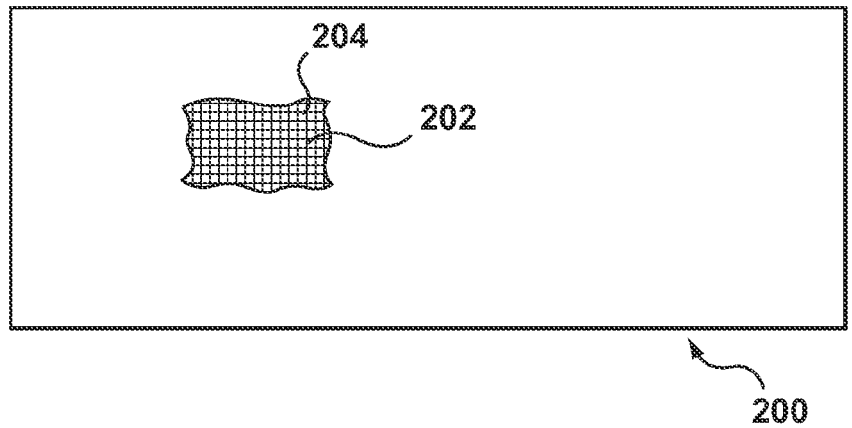
FIGS. 3-7 illustrate schematically an embodiment of a method of making an endoluminal prosthesis from a flat sheet of woven material.

Referring now to the FIGS. 3-6, wherein components are labeled with like numerals throughout the several figures, an embodiment of a method of making a an endoluminal prosthesis 220 including a graft material 210 with warp yarns 202 disposed at an angle relative to a longitudinal axis 218 of the prosthesis 220 is disclosed. In particular, as shown in FIG. 3, a woven sheet of material 200 is utilized. Woven sheet of material 200 may be made from yarns made from biocompatible materials known to those skilled in the art as suitable for use in an endoluminal prosthesis, including but not limited to yarns made from polyester, polytetrafluoroethylene (PTFE), polypropylene, stainless steel, or nitinol. Woven sheet of material 200 consists of warp or end yarns 202 and weft, fill or pick yarns 204 interlaced at right angles (perpendicular) to each other, as shown in FIG. 1. Woven sheet of material 200 may be a plain weave or other weaves suitable for a graft material. The warp yarn 202 and weft yarn 204 may be the same material or different materials. For example, and not by way of limitation, one of the yarns may be a radiopaque material or may be a conventional material with radiopaque material added thereto.

Figure 4:
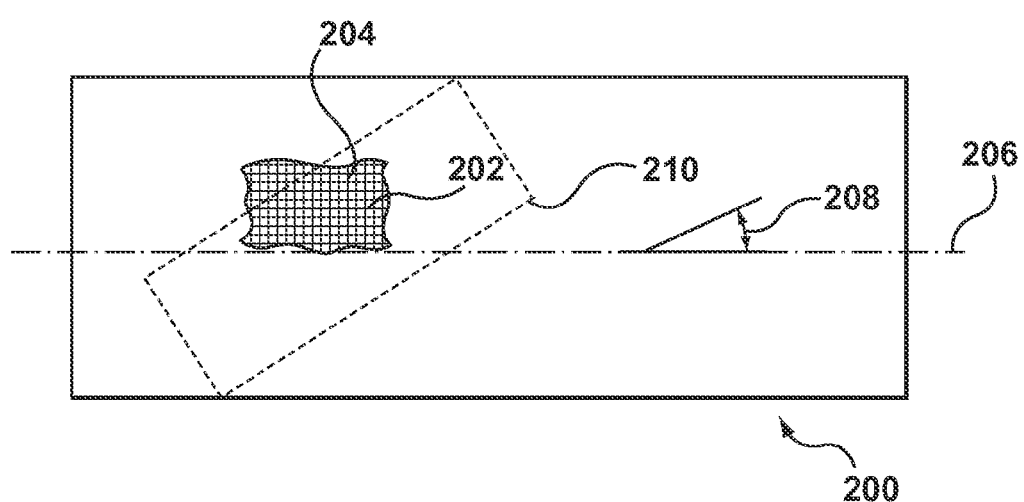

A graft material section 210 is then cut from woven sheet of material 200 at an angle 208 relative to a longitudinal axis 206 of the woven sheet of material 200, as shown schematically in FIG. 4. Graft material section 210 may be cut using devices known to those skilled in the art, including but not limited to laser cutters. In the embodiment shown, graft material section 210 is generally rectangular. However, graft material section 210 may be any shape suitable to be made into a generally tubular or bifurcated tubular endoluminal prosthesis. Angle 208 is preferably between 15 degrees and 75 degrees, 30 degrees and 60 degrees, or approximately 45 degrees, depending on the desired characteristics of the endoluminal prosthesis.

Figure 5:
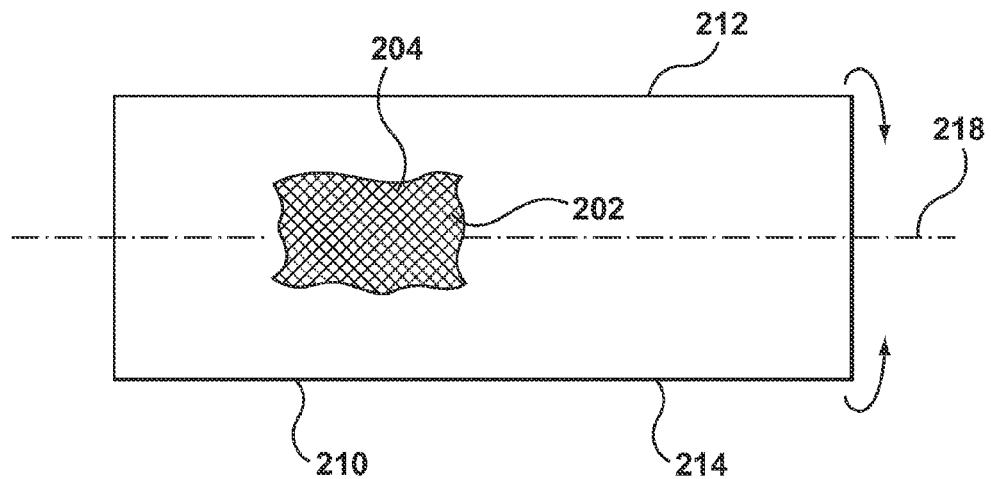

Graft material section 210 as shown in FIG. 5 thus includes warp yarns 202 and weft yarns 204 disposed generally perpendicular to each other, but disposed at other than right angles relative to a longitudinal axis 218 of the graft material section 210. Next, edges 212, 214 are rolled towards each other around longitudinal axis 218, as indicated by the arrows in FIG. 5, to form a generally tubular, endoluminal prosthesis 220, as shown schematically in FIG. 6. Ends 212, 214 may be attached to each other at seam 216 using stitching, fusion, adhesives or other methods or devices known to those skilled in the art.

Figure 7:
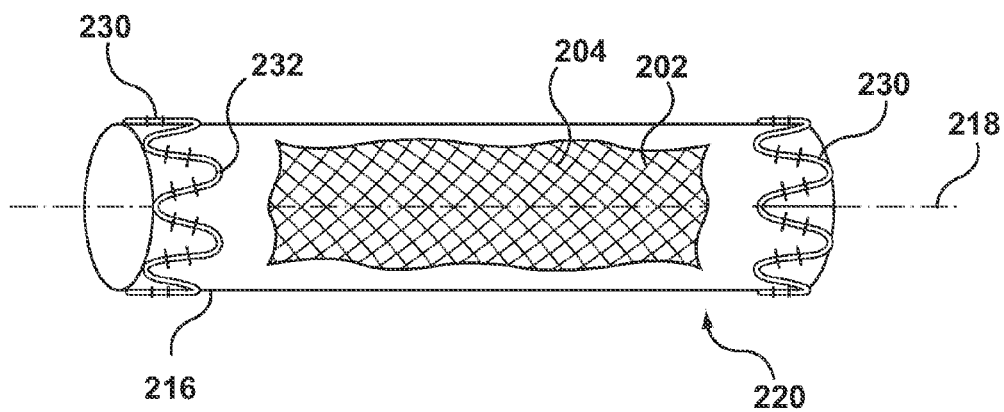

Stents 230 may be attached to graft material 210, as shown in FIG. 7. Stents 230 may be attached to graft material 210 before or after securing opposing edges 212, 214 to each other to form endoluminal prosthesis 220. Further, although stents 230 are shown attached to an outer surface of the graft material 210, stents 230 could alternatively be attached to an inner surface of the graft material 210. Stents 230 are shown attached to the graft material 210 using stitching 232. However, stents 230 may be attached to graft material 210 by other methods or devices known to those skilled in the art, such as, but not limited to, adhesives.

Figure 6:
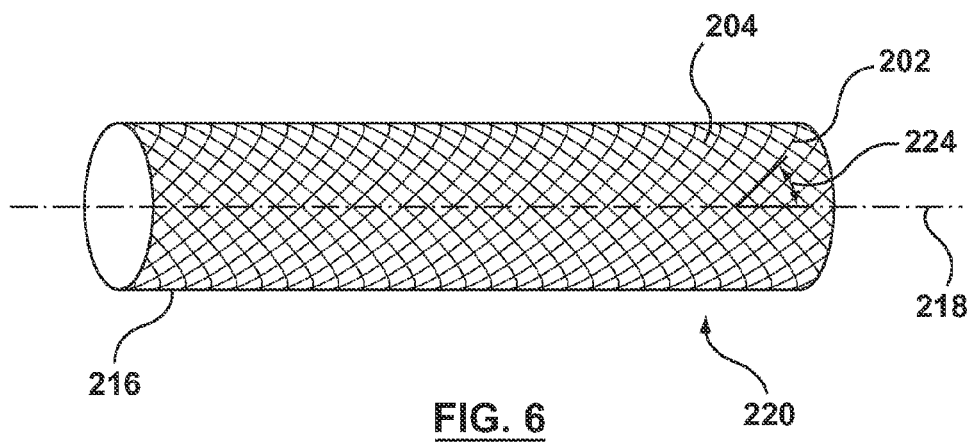

The endoluminal prosthesis 220 shown in FIG. 6 thus includes warp yarns 202 disposed at an angle 224 relative to longitudinal axis 218 of the prosthesis 220. Angle 224 is preferably between 15 degrees and 75 degrees, 30 degrees and 60 degrees, or approximately 45 degrees, depending on the desired characteristics of the endoluminal prosthesis. Those skilled in the art would recognize that although the angle 224 is defined in terms of the angle between the warp yarns 202 and longitudinal axis 218, the angle could also be defined in terms of the weft yarns 204 and longitudinal axis 218, between the weft yarns 204 and a circumferential axis, or between the warp yarns 202 and a circumferential axis.

Figure 8:
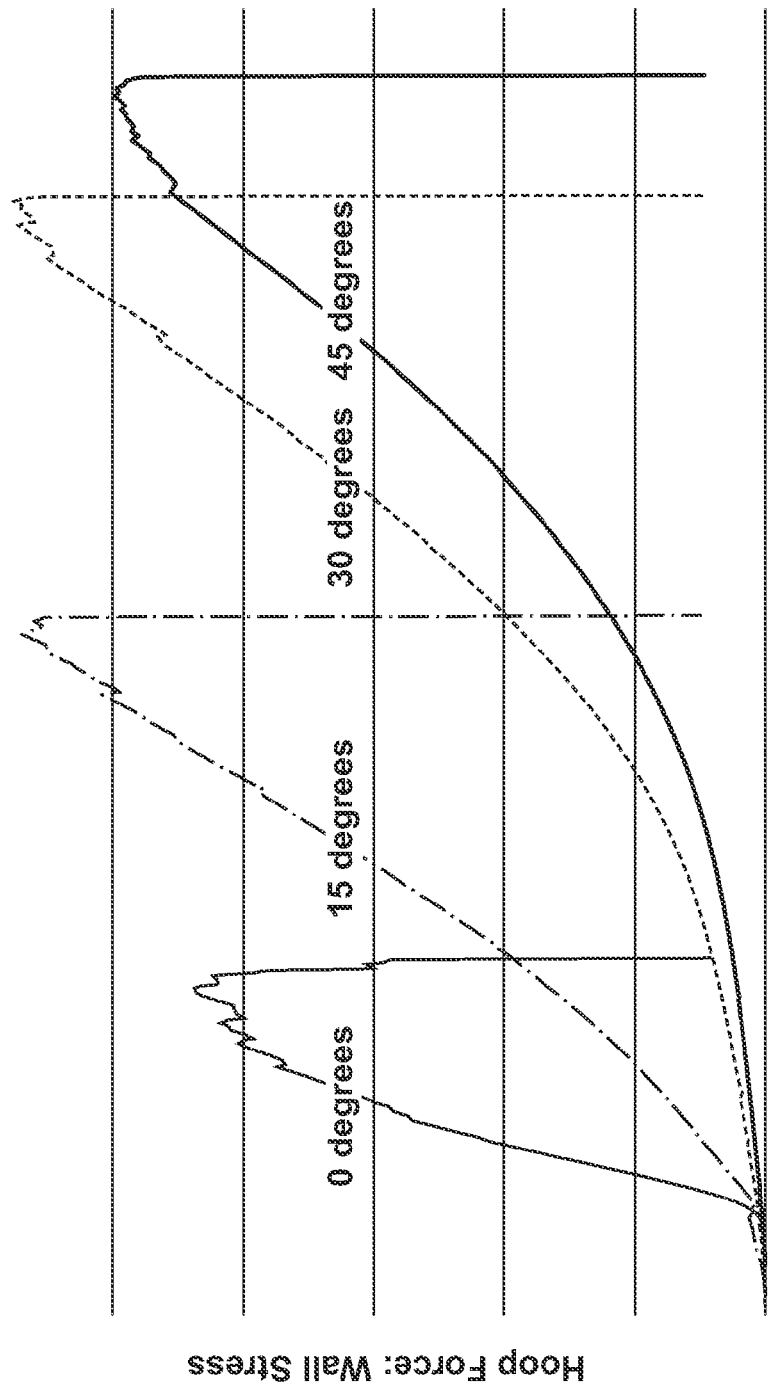
FIG. 8 is a chart illustrating stresses in a woven graft material of a tubular prosthesis as a function of radial displacement of the prosthesis for prostheses with warp yarns disposed at various angles relative to the longitudinal axis.

By orienting the warp yarns 202 and weft yarns 204 other than parallel and perpendicular to the longitudinal axis and the circumferential axis, the prosthesis 220 exhibits enhanced flexibility, a smaller packing profile (i.e., a smaller outer diameter in the radially contracted configuration), and a greater resistance to internal radial pressure. When warp yarns 202 and weft yarns 204 are oriented other than parallel and perpendicular to the graft longitudinal axis, longitudinal and radial loads are shared by both sets of yarns and the graft is capable of great deformations in either the radial or longitudinal direction. As an example, consider an internal pressure applied by a compliant balloon suitable for perioperative stent graft modeling. In a traditional tubular woven graft with the warp yarns parallel to the longitudinal axis and the weft yarns perpendicular to the longitudinal axis (i.e., circumferentially), circumferential weft yarns immediately draw taught and begin to develop tensile stresses which are in turn exerted on the seam. In the case that the warp and weft yarns are each oriented at 45 degrees to the graft axis, the graft is able to deform while yarns re-align in the direction of the force. The graft is able to grow substantially in diameter under much smaller pressures and tensile stresses. For a given balloon inflation volume, a prosthesis fabricated from angle oriented graft material will develop less internal pressure and stress. By this means the seam, and overall graft integrity, is preserved from potential over-pressurization during balloon modeling. FIG. 8 illustrates this reduced wall stress, wherein the line marked "0 degrees" indicates a tubular graft with the warp yarns parallel to the longitudinal axis. As can be seen in FIG. 8, the wall stress increases at a smaller radial displacement in the "0 degree" embodiment than when the warp yarns are oriented at an angle of 15 degrees, 30 degrees, or 45 degrees relative to the longitudinal axis of the graft.

The endoluminal prosthesis 220 shown in FIG. 6 is not limited to the simple, tubular configuration shown. Instead, endoluminal prosthesis 220 can be formed into many shapes known to those skilled in the art, including but not limited to, bifurcated configurations, configurations with fenestrations for side branches, configurations with side branches, modular configurations, etc. Endoluminal prosthesis 220 includes a radially contracted or delivery configuration (not shown) for delivery and a radially expanded or deployed configuration for placement in a vessel, as known to those skilled in the art. Endoluminal prosthesis may be self-expanding from the radially contracted configuration to the radially expanded configuration, such as through the use of self-expanding stents coupled thereto, or may be balloon expandable, as known to those skilled in the art. Devices and methods for delivering and deploying endoluminal prosthesis 220 to a treatment site are known to those skilled in the art.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of making an endoluminal prosthesis comprising the steps of:
using a flat sheet of woven material, the woven material including warp yarns and weft yarns interlaced at right angles to each other;
cutting a graft material from the flat sheet of woven material such that the graft material includes a graft material longitudinal axis and the warp yarns are disposed at a first angle relative to the graft material longitudinal axis such that the warp yarns and graft material longitudinal axis are not parallel or perpendicular to each other; and
rolling opposing edges of the graft material towards each other and securing the opposing edges together to form a tubular shape of the endoluminal prosthesis including a prosthesis longitudinal axis, wherein a projection of the warp yarns onto the longitudinal axis of the prosthesis at the location of the warp yarns is disposed at a second angle relative to the prosthesis longitudinal axis, wherein the second angle is such that the projection of the warp yarns at the location is not parallel or perpendicular to the prosthesis longitudinal axis.

2. The method of claim 1, wherein the first angle and the second angle are substantially the same.

3. The method of claim 1, wherein the second angle is in the range of 15 degrees to 75 degrees.

4. The method of claim 1, wherein the second angle is in the range of 30 degrees to 60 degrees.

5. The method of claim 1, wherein second angle is approximately 45 degrees.

6. The method of claim 1, wherein the step of securing the opposing edges together comprises sewing the edges together or fusing the edges together or adhesively securing the edges together.

7. The method of claim 1, wherein the step of cutting the graft material from the flat sheet of woven material comprises laser cutting.

8. The method of claim 1, further comprising the step of attaching at least one stent to the graft material.

9. The method of claim 1, wherein the flat sheet of woven material is constructed from yarns made from polyester, polytetrafluoroethylene, polypropylene, stainless steel wire, or nitinol wire.

\* \* \* \* \*